United States Patent [19]

Bradford

[11] Patent Number: Plant 5,438

[45] Date of Patent: Apr. 16, 1985

[54] NECTARINE TREE - EARLY DIAMOND

[76] Inventor: Norman G. Bradford, 11875 E. Savana Rd., LeGrand, Calif. 95333

[21] Appl. No.: 518,964

[22] Filed: Aug. 1, 1983

[51] Int. Cl.[3] ..... A01H 5/03
[52] U.S. Cl. ..... Plt./41
[58] Field of Search ..... Plt./41

*Primary Examiner*—Robert E. Bagwill
*Attorney, Agent, or Firm*—Vergil L. Gerard

[57] ABSTRACT

The present invention relates to a nectarine tree and more particularly to a new and distinct variety broadly characterized by a large, vigorous, very productive, early blooming tree which regularly bears medium size, globose fruit with almost solid red skin which becomes almost maroon when fully ripe and yellow-gold flesh which ripens with the earliest commercial varieties and is of good eating quality and excellent firmness for shipping and long shelf life. The cultivar name of this nectarine tree is Early Diamond.

1 Drawing Figure

BACKGROUND OF THE VARIETY

The instant variety most nearly resembles its parent plant Aurelio Grand (U.S. Plant Pat. No. 3,755) but is an improvement thereon by being shipping ripe almost a week before Aurelio Grand, and having a dark, overall red skin coloration.

The instant variety was propogated by us at Bradford Farms in Merced County, Calif., by pollinating an unnamed seedling with the Aurelio Grand nectarine. The instant variety was thereafter asexually reproduced by budding in 1979 and the resulting plant and fruit characteristics were true to the original mutation in all respects.

DRAWING

The accompanying photograph shows the characteristics of the whole fruit in skin color and form, and a characteristic fruit divided at its suture plane showing flesh color, stone, and stone cavity, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at full commercial maturity in the 1982 growing season. All color plate identifications are by reference to Dictionary of Color, 1950 (2d ed.) by Maerz and Paul.

TREE

General: Large, vigorous and dense, spreading with age and crop, with shape and density determined by pruning. Very productive and regular bearing.

Trunk: The trunk is of medium thickness, and smooth surface texture. Older bark is brownish in color with a medium number of medium to small lenticles.

Branches: Medium in size and surface texture.

LEAVES

Measurements are from medshoot leaves from vigorous shoots.

Size: Average length, 5", average width, $1\frac{1}{2}$".

Form: Oblanceolate. Acuminate, base acute. Tip acute and finely pointed.

Color:

*Top side.*—Dark Green (23-L-10)

*Under side.*—Lighter Green (22-k-8).

Margin: Finely serrate.

FLOWERS

Buds: Large size, hardy, free from stem; medium length, pointed at tip.

Flowers: Early blooming, first week in March; full bloom by March 10; large size, pink in color.

FRUIT

Shipping ripe when described.

Maturity: May 20th in area of propagation.

Size: Uniform, medium. Axial diameter, $2\frac{1}{8}$", traverse in suture plane, 2".

Form: Symmetrical, globose.

Suture: Shallow, extends from base to apex on one side, faint to almost invisible on opposite side, Ventral surface: Strongly rounded, liped from midpoint toward base, slight lip from midpoint to apex; lips mostly equal.

Skin color: Cheeks Tapestry Red (7-J-5), shoulders Pomergranate (6-L-3), becoming almost overall maroon color at full maturity. Ground color yellow (19-J-1) to (18-K-1), showing through shoulder area at time of description. Pubescence lacking.

Stone cavity: Elongated in suture plane $1\frac{3}{8}$", breadth $\frac{7}{8}$".

Flesh: Very light yellow-gold (10-I-4) to Corn (10-J-6). No red coloration bleeding into flesh from skin; Yellow color constant all the way to cavity. Stone cavity color Honeysweet (11-J-5).

Stem: $\frac{1}{4}$" To $\frac{3}{8}$" in length.

Amygdalin: Scarce, moderate juice.

*Texture.*—Extremely firm, fine, crisp.

Fibres: Medium, fine and tender. Ripens evenly.

*Flavor.*—Subacid.

*Eating quality.*—Very good.

STONE

Shape: Oval, base straight, hilum oval to oblong, apex rounded, sides equal, apex rounded.

*Surface.*—Irregularly furrowed overall; ridged near base to apex, ridges jagged.

*Color.*—Buff (11-K-1). Tendency to split if not girdled.

*Kernel.*—Ovate, sweet; length 0.70", width 0.40"; scant amygdalin.

USE

Market — fresh and long distance shipping. Extraordinary firmness allows long distance shipping with excellent shelf life. Keeping quality excellent, good resistance to insects and disease.

I claim:

1. A very early fresh market nectarine distinguishable by its full red color, excellent firmness, excellent shelf life and shipping quality, and good eating, which ripens six to seven days before the parent plant Aurelio Grand (U.S. Plant Pat. No. 3,755) and among earliest commercial varieties.

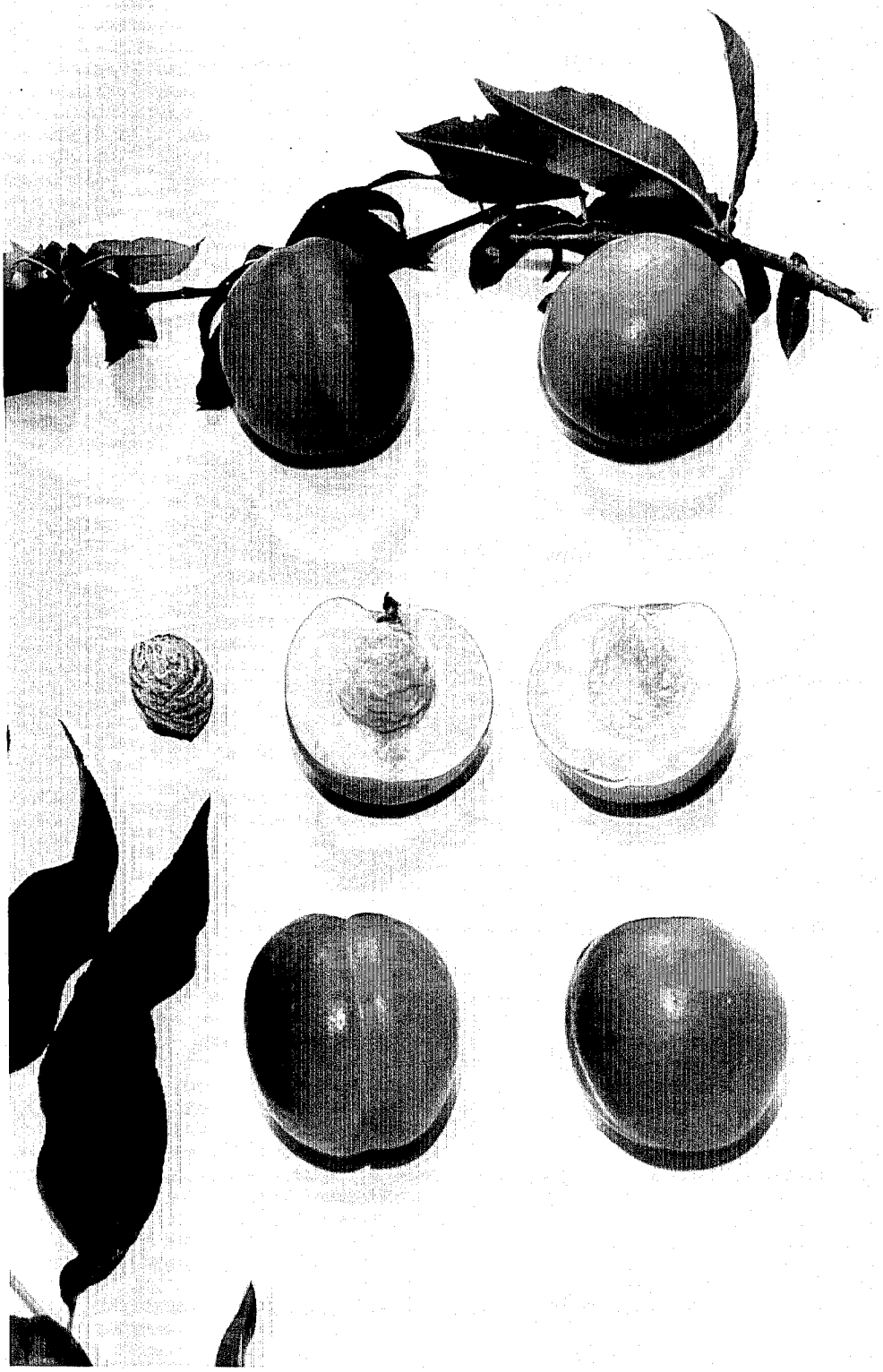

* * * * *